(12) United States Patent
Gatherar et al.

(10) Patent No.: US 8,066,911 B2
(45) Date of Patent: Nov. 29, 2011

(54) METHOD OF IMPROVING FLOWABILITY OF ADIPIC ACID

(75) Inventors: Kevin Gatherar, West Auckland (GB); Richard C. Hill, Toronto (CA); Julien Hillman, Bedale (GB); James E. McIntosh, Beaumont, TX (US)

(73) Assignee: Invista North America S.A.R.L., Wilmington, DE (US)

( * ) Notice: Subject to any disclaimer, the term of this patent is extended or adjusted under 35 U.S.C. 154(b) by 0 days.

(21) Appl. No.: 12/183,685

(22) Filed: Jul. 31, 2008

(65) Prior Publication Data

US 2010/0025635 A1 Feb. 4, 2010

(51) Int. Cl.
*C09K 3/00* (2006.01)
*A23L 1/00* (2006.01)
*A61L 2/00* (2006.01)
*A61L 2/04* (2006.01)
*A61L 9/00* (2006.01)
*A61L 11/00* (2006.01)
*C23F 11/00* (2006.01)
*C07C 61/00* (2006.01)
*C07C 53/00* (2006.01)
*C07C 55/00* (2006.01)

(52) U.S. Cl. ........ 252/384; 252/380; 252/381; 252/383; 422/1; 562/400; 562/512; 562/590

(58) Field of Classification Search .................. 252/384, 252/380, 381, 383; 562/540, 400, 512, 590; 422/1
See application file for complete search history.

(56) References Cited

U.S. PATENT DOCUMENTS

| 3,459,798 A | | 8/1969 | Lassiter | |
|---|---|---|---|---|
| 3,476,804 A | * | 11/1969 | Kurt et al. | .................. 562/530 |
| 5,025,087 A | | 6/1991 | Williams, III | |
| 5,502,247 A | * | 3/1996 | Bartos et al. | .................. 562/486 |

* cited by examiner

*Primary Examiner* — Lorna M Douyon
*Assistant Examiner* — Tanisha Diggs

(57) ABSTRACT

A method of improving flowability of adipic acid includes adding to the adipic acid at a relatively low temperature a flowability improving agent, such as an acyclic saturated monobasic acid containing 10 to 22 carbon atoms or an acyclic saturated dibasic acid containing 10 to 14 carbon atoms.

9 Claims, No Drawings

METHOD OF IMPROVING FLOWABILITY OF ADIPIC ACID

FIELD OF THE INVENTION

This disclosure is directed to a method of improving flowability of adipic acid, by adding to the adipic acid at a relatively low temperature an agent which improves flowability of adipic acid (also referred to herein as a "flowability improving agent").

BACKGROUND OF THE INVENTION

Description of Related Art

Adipic acid can be used in various industrial applications, e.g., in the manufacture of polyamides and as a food additive. Adipic acid is a white, crystalline solid which may be prepared by oxidizing cyclohexane to cyclohexanol and cyclohexanone, followed by further oxidation of the alcohol and the ketone with nitric acid. After the oxidation of the alcohol and ketone with nitric acid, a purification stage of adipic acid production is carried out. Vacuum is applied to remove a proportion of the nitric acid and water; and as the temperature decreases, adipic acid is preferentially crystallized from the mixture. There are usually at least three stages of crystallization to obtain the adipic acid of desired purity. The process stream of the last stage is a slurry of adipic acid crystals in essentially water (with trace amounts of nitric acid present). The slurry is then refined by centrifuging and drying the solids in a dryer, such as a rotary drier or a fluid bed dryer, at 95-100° C. to produce the final adipic acid product. Usually, this adipic acid is conveyed from the dryer to a packing station, such as by screw conveying, to be packaged in suitable containers, such as rail cars, road containers or bags. Adipure® grade adipic acid is one commercially available adipic acid product. Also, see, Lassiter, U.S. Pat. No. 3,459,798, incorporated herein by reference.

After adipic acid is prepared, it is usually necessary to store it in large quantity lots or ship it to other locations before it can be used in a manufacturing process. When stored, adipic has the propensity to form hard lumps (which may be large), particularly at high temperature and humidity, which are difficult to break up and may cause bridging, and reduce flowability at ultimate users' (i.e., customers') sites. If that occurs, the large hard lumps (agglomerations) of adipic acid must be reduced in order for the adipic acid to be processed. The process of reducing, e.g., by breaking up, the hard lumps of adipic acid is a costly and time-consuming endeavor.

Lassiter, U.S. Pat. No. 3,459,798, discusses a method of preventing caking of adipic acid by adding to the adipic acid a relatively small amount (25-200 ppm.) of an anticaking agent as a solid or as an aqueous slurry during slurry refining, during drying, by hot dry-blending or by spray drying. Lassiter's preferred method of incorporating the anticaking agent into the adipic acid involves adding to the adipic acid an aqueous slurry of the anticaking agent, prior to drying the adipic acid. According to Lassiter, the anticaking agent is added at a temperature of 50-100° C., such as 95-100° C.

The anticaking agents disclosed by Lassiter include higher molecular weight organic acids, which can be straight-chained or branch-chained, such as acyclic saturated monobasic acids having 10-22 carbons, or acyclic saturated dibasic acids of 10-14 carbon atoms. Exemplary acids disclosed by Lassiter are decanoic acid, undecanoic acid, lauric acid, tridecanoic acid, myristic acid, pentadecvlic acid (sic., pentadecylic acid), palmitic acid, margaric acid, stearic acid, nondecnoic acid (sic., nonyldecanoic acid), arachic acid, behenic acid, decanedioic acid, undecanedioic acid, dodecanedioic acid (DDDA), and tetradecanedioic acid.

Williams, III, U.S. Pat. No. 5,025,087, discloses nylon 66 filaments having improved dyeability, which include a small content, such as about 50 to about 150 ppm, of dodecanedioic acid (DDDA).

SUMMARY OF THE INVENTION

One embodiment of this disclosure is directed to a method of improving flowability of adipic acid, including adding to the adipic acid a flowability improving agent, at a relatively low temperature, about 20 to about 35° C. The flowability improving agent is an acyclic saturated monobasic acid containing 10 to 22 carbon atoms or an acyclic saturated dibasic acid containing 10 to 14 carbon atoms, such as DDDA.

We realized that the addition of an agent that improves flowability of adipic acid at the high temperatures, which were taught in prior art for anticaking agents, may present several issues and disadvantages. For example, a flowability improving agent, such as DDDA, added at the high temperatures, e.g., in the dryer, may result in the DDDA being recycled via fines recovery, together with adipic acid fines, back to the main plant. Since the DDDA is less soluble in water than adipic acid, the DDDA can build up on the inner walls and cause a constriction (i.e., potential fouling) in the process flow. Further, DDDA could be recycled back into the purge system where there is the potential for it to cause a serious hazardous reaction which could result in a process incident. Thus, in embodiments of this invention, the flowability improving agent is added to the adipic acid at a relatively low temperature.

DETAILED DESCRIPTION

All numerical values in this disclosure are understood as being modified by "about". All singular forms of flowability improving agents, acids or other components described herein including (without limitations) components of the compositions are understood to include plural forms thereof and vice versa.

In this application, whenever a composition, a flowability improving agent or a group of elements is preceded with the transitional phrase "comprising", it is understood that we also contemplate the same composition, flowability improving agent or group of elements with transitional phrases "consisting essentially of", "consisting", "selected from the group of consisting of", or "is" preceding the recitation of the composition, flowability improving agent or elements, and vice versa.

Without wishing to be bound by any operability theory, adipic acid has the propensity to form hard lumps which are difficult to break up and can cause flowability issues at customers' sites. It is believed that the addition of the flowability improving agent, such as DDDA, as described herein, does not prevent lump formation, but it prevents the lumps from becoming hard, i.e., the lumps remain more friable. As a result, the customary, normal action of discharging the adipic acid from the containers or bags easily breaks the lumps, thereby improving flowability. Without the addition of the flowability improving agent, the lumps do not break up and require other measures to break them up, such as using vibrating hammers and/or manual tools.

The acids used as the agents that improve flowability may have linear or branched carbon chains. Suitable acids are decanoic acid, undecanoic acid, lauric acid, tridecanoic acid, myristic acid, pentadecylic acid, palmitic acid, margaric acid, stearic acid, nonyldecanoic acid, arachic acid, behenic acid, decanedioic acid, undecanedioic acid, dodecanedioic acid (also referred to herein as "1,12-dodecanedioic acid"), tetradecanedioic acid or a mixture thereof The flowability improving agent may be added in any suitable form, such as a dry powder, e.g., as a finely ground powder, milled to have particle size of less than about 75 micron, such as less than about 40 micron. The flowability improving agent may be added at any point in the process which makes the adipic acid, where the temperature of the process stream is within the range of about 20 to about 35° C., such as of about 20 to about 30° C., e.g., about 25° C. Advantageously, the flowability improving agent is added in such manner as to promote thorough mixing and contact with the adipic acid. For example, the flowability improving agent can be added to the conveyor, such as a screw conveyor, downstream of the dryer, which carries the adipic acid to the packing section. In one embodiment, the flowability improving agent is added to adipic acid downstream of the drier, at such point in the process that the temperature of the adipic acid is not higher than about 35° C. For example, the flowability improving agent may be added to the adipic acid downstream of the drier and before the adipic acid is placed in containers for shipment to customers. In one embodiment, the flowability improving agent is added in the vicinity of the exit of the dryer, e.g., at the exit of the dryer. The flowability improving agent is added in such an amount that the resulting adipic acid has a substantially improved flowability (as compared to the adipic acid without the flowability improving agent) and/or is substantially free flowing. The term "substantially free flowing" means that the lumps in the adipic acid are prevented from becoming hard and thus the lumps are substantially friable, which allows the adipic acid material to flow substantially without manual intervention. The flowability improving agent is added to the adipic acid in the amount of about 50 to about 600 ppm, such as about 150 to about 250 ppm, or about 100 to about 200 ppm, or about 150 ppm, based on the adipic acid. The adipic acid to which the flowability improving agent is added is, in one embodiment, pure adipic acid, i.e., 99.5% or higher percentage, such as 99.7% adipic acid on a water-free basis.

The following examples illustrate the present disclosure and the advantages thereof without limiting the scope of this disclosure or the claims.

Example 1

No Flowability Improving Agent

Adipic acid is produced in a conventional method described above, with no flowability improving agent added. The adipic acid product is stored for 10 days at 25° C. and 100% relative humidity. It is expected that if such adipic acid product were to be shipped to customers, significant hardening of the lumps would be observed and breaking up of the adipic acid would be necessary to make it substantially free flowing.

Example 2

Flowability Improving Agent Added

Adipic acid is produced in a conventional method described above. After the dried adipic acid leaves the dryer and is cooled to about 30° C., about 200 ppm of dodecanedioic acid is added to the adipic acid. The thus-modified adipic acid product is stored for 10 days at 25° C. and 100% relative humidity. It is expected that if such adipic acid product were to be shipped to customers, no significant hardening of the lumps would be observed and breaking up of the adipic acid would not be necessary to make it substantially free flowing.

All documents described or mentioned herein are incorporated by reference herein in their entirety, including any priority documents and/or testing procedures. As is apparent from the foregoing general description and the specific embodiments, while forms of the disclosure have been illustrated and described, various modifications can be made without departing from the spirit and scope thereof. Accordingly, it is not intended that the invention be limited thereby. Likewise, the term "comprising" is considered synonymous with the term "including" for purposes of Australian or the U.S.A. law.

The invention claimed is:

1. A method of improving flowability of adipic acid comprising adding to the adipic acid downstream of a dryer used in a process for making said adipic acid and at a temperature of about 20 to about 35° C., an agent that improves flowability of the adipic acid, which agent is an acyclic saturated monobasic acid containing 10 to 22 carbon atoms or an acyclic saturated dibasic acid containing 10 to 14 carbon atoms wherein the agent is added as a dry powder.

2. A method of claim 1, wherein said flowability improving agent is decanoic acid, undecanoic acid, lauric acid, tridecanoic acid, myristic acid, pentadecylic acid, palmitic acid, margaric acid, stearic acid, nonyldecanoic acid, arachic acid, behenic acid, decanedioic acid, undecanedioic acid, dodecanedioic acid, tetradecanedioic acid or a mixture thereof.

3. A method of claim 1, wherein said flowability improving agent is 1,12-dodecanedioic acid.

4. A method of claim 1, wherein said flowability improving agent is added in the vicinity of the exit of a dryer used in a process for making the adipic acid.

5. A method of claim 4, wherein said flowability improving agent is added at the exit of the dryer.

6. A method of claim 1, wherein said flowability improving agent is added to a conveyor downstream of a dryer used in a process for making the adipic acid.

7. A method of claim 1, wherein said conveyor is a screw conveyor.

8. A method of claim 1, wherein the adipic acid is pure adipic acid.

9. A method of claim 1, wherein about 50 ppm to about 600 ppm of said flowability improving agent is added to the adipic acid, based on the adipic acid.

* * * * *